United States Patent
Matsusaki et al.

(10) Patent No.: US 8,828,679 B2
(45) Date of Patent: Sep. 9, 2014

(54) METHOD AND KIT FOR DETECTING BIOLOGICAL SIGNAL OF THREE-DIMENSIONAL CELL CULTURE MATERIAL

(75) Inventors: Michiya Matsusaki, Osaka (JP); Mitsuru Akashi, Osaka (JP); Kazunori Okano, Hyogo (JP)

(73) Assignee: Japan Science and Technology Agency, Saitama (JP)

( * ) Notice: Subject to any disclaimer, the term of this patent is extended or adjusted under 35 U.S.C. 154(b) by 240 days.

(21) Appl. No.: 13/128,360

(22) PCT Filed: Nov. 10, 2009

(86) PCT No.: PCT/JP2009/069124
§ 371 (c)(1),
(2), (4) Date: May 9, 2011

(87) PCT Pub. No.: WO2010/055829
PCT Pub. Date: May 20, 2010

(65) Prior Publication Data
US 2011/0217726 A1    Sep. 8, 2011

(30) Foreign Application Priority Data
Nov. 11, 2008 (JP) .................. 2008-289011

(51) Int. Cl.
*C12Q 1/02* (2006.01)
*G01N 33/50* (2006.01)
*G01N 33/543* (2006.01)

(52) U.S. Cl.
CPC ........ *G01N 33/5032* (2013.01); *G01N 33/5088* (2013.01); *G01N 33/54313* (2013.01)
USPC ........................................................... 435/29

(58) Field of Classification Search
None
See application file for complete search history.

(56) References Cited

U.S. PATENT DOCUMENTS

| 6,001,643 | A | 12/1999 | Spaulding |
| 2002/0192636 | A1 | 12/2002 | Guarino et al. |
| 2004/0030406 | A1 | 2/2004 | Ochi et al. |
| 2007/0172812 | A1 | 7/2007 | Ochi et al. |
| 2007/0207540 | A1 | 9/2007 | Akashi et al. |

FOREIGN PATENT DOCUMENTS

| CN | 1477979 | 2/2004 |
| EP | 1 626 278 | 2/2006 |
| JP | 2006-042671 | 2/2006 |
| JP | 2007-082528 | 4/2007 |
| JP | 2007-228921 | 9/2007 |
| JP | 2007-267727 | 10/2007 |
| JP | 2007-279015 | 10/2007 |
| WO | 2007/035301 | 3/2007 |

OTHER PUBLICATIONS

Petroll et al., Cell Motility and the Cytoskeleton vol. 55: 254-264, 2003.*
Liu et al., Colloids and Surfaces B: Biointerfaces vol. 58, pp. 8-13, available online Aug. 22, 2006.*
Yang, et al., "Microbioreactors for high-throughput cytotoxicity assays", Current Opinion in Drug Discovery and Development, Current Drugs, vol. 11, No. 1, Jan. 2008, pp. 111-127.
Matsusaki, et al., "The construction of 3D-engineered tissues composed of cells and extracellular matrices by hydrogel template approach", Biomaterials, vol. 28, No. 17, Mar. 2007, pp. 2729-2737.
Acosta, et al., "Fluorescent microparticles for sensing cell microenvironment oxygen levels within 3D scaffolds", Biomaterials, vol. 30, No. 17, Jun. 2009, pp. 3068-3074.
Matsusaki, et al., "Fabrication of Cellular Multilayers with Nanometer-Sized Extracellular Matrix Films", Angew. Chem. Int. Ed., vol. 46, 2007, pp. 4689-4692.
Nakahara, et al., "Fabrication and enzymatic degradation of fibronectin-based ultrathin films", J. Biomater. Sci. Polymer Edn, vol. 18, No. 12, 2007, pp. 1565-1576.
Shimizu, et al., "Fabrication of Pulsatile Cardiac Tissue Grafts Using a Novel 3-Dimensional Cell Sheet Manipulation Technique and Temperature-Responsive Cell Culture Surfaces", Circulation Research, 2002, 90, e40-e48.
Co, et al., "Biocompatible Micropatterning of Two Different Cell Types", J. Am. Chem. Soc., vol. 127, 2005, pp. 1598-1599.
Tan, et al., "Layer-by-layer microfluidics for biomimetic three-dimensional structures", Biomaterials, vol. 25, 2004, pp. 1355-1364.
Kojima, et al., "Detection and Imagin of Nitric Oxide with Novel Fluorescent Indicators: Diaminofluoresceins", Analytical Chemistry, vol. 70, No. 13, Jul. 1998.
Takahashi, et al., "Measurement of Intracellular Calcium", Physiol Rev, vol. 79, 1999, pp. 1089-1125.

* cited by examiner

*Primary Examiner* — Allison Ford
*Assistant Examiner* — Yvonne Pyla
(74) *Attorney, Agent, or Firm* — Hamre, Schumann, Mueller & Larson, P.C.

(57) ABSTRACT

Disclosed is a method for detecting a biological signal of a three-dimensional cell culture construct. The method for detecting a biological signal of a three-dimensional cell culture construct includes: providing a three-dimensional cell culture construct that contains at least two cell layers laminated to each other and a sensor particle capable of detecting a biological signal; and observing the sensor particle optically. Preferably, the three-dimensional cell culture construct contains an extracellular matrix including a combination of a protein or polymer having an RGD sequence and a protein or polymer that interacts with the protein or polymer having the RGD sequence, or a combination of a protein or polymer that is positively charged and a protein or polymer that is negatively charged.

8 Claims, 6 Drawing Sheets

METHOD AND KIT FOR DETECTING BIOLOGICAL SIGNAL OF THREE-DIMENSIONAL CELL CULTURE MATERIAL

TECHNICAL FIELD

The present invention relates to a method for detecting a biological signal of a three-dimensional cell culture construct and a detection kit used in the same.

BACKGROUND ART

Cells exhibit various functions, including a function of transmitting information for normally functioning as an organism.

As techniques for observing states of cells, signals produced by cells, responses of cells to drugs or the like, there are the following: a technique of extracting DNAs and proteins from cells after stimulating the cells in some way and analyzing them; a technique of measuring substances produced by cells or substances present on surfaces or inside of cells using fluorescent compounds or the like (Patent Document 1); and a technique of observing shapes of cells and measuring the electric potential change of cells optically or electrochemically while culturing the cells on a cell-culturing microarray provided with electrodes and the like (Patent Document 2).

Meanwhile, as techniques for laminating cells three-dimensionally there are the following: a technique of forming a three-dimensional laminate by repeating the step of forming an extracellular matrix and a cell layer alternately (Patent Document 3, Non-Patent Documents 1 and 2); a cell sheet technique of laminating two-dimensional cell sheets that are prepared beforehand by culturing cells in a sheet form (Non-Patent Document 3); a technique of laminating cells using chitosan thin films (Non-Patent Document 4); and a technique of laminating cells by pouring a microfluid containing cells and extracellular matrices in a pass (Non-Patent Document 5).

PRIOR ART DOCUMENT

Patent Document

Patent Document 1; JP 2007-279015A
Patent Document 2: JP 2006-42671 A
Patent Document 3: JP 2007-228921 A

Non-Patent Document

Non-Patent Document 1: M. Matsusaki et al., Angew. Chem. Int. Ed. 2007, 46, 4689
Non-Patent Document 2: Y Nakahara et at, J. Biomater Sci. Polymer Edn. 2007, 18, 1565
Non-Patent Document 3: T. Okano et al., Circ Res. 2002, 90. 40
Non-Patent Document 4: C. C. Co et al., J. Am. Chem. Soc. 2005, 127, 1598
Non-Patent Document 5: W Tan. Et at, Biomaterials 2004, 25, 1355

DISCLOSURE OF INVENTION

Problem to be Solved by the Invention

However, in such conventional methods, the responses of individual cells can be evaluated, but responses as a tissue or responses of cells in a tissue cannot be evaluated in vitro. Further, a determination of a diffused position of biological signals produced by cells and a quantitative evaluation of biological signals cannot be achieved. Therefore, the present invention provides a method for detecting a biological signal of a three-dimensional cell culture construct.

Means for Solving Problem

The present invention relates to a method for detecting a biological signal of a three-dimensional cell culture construct, including: providing a three-dimensional cell culture construct that contains at least two cell layers laminated to each other and a sensor particle capable of detecting a biological signal; and observing the sensor particle optically.

Effect of the Invention

According to the present invention, for example, it is possible to detect a biological signal of a cell culture construct laminated three-dimensionally with ease. Further, for example, the present invention preferably provides an effect of evaluating responses as a tissue or responses of cells in a tissue in vitro.

DESCRIPTION OF PREFERRED EMBODIMENT

Figure 1A:
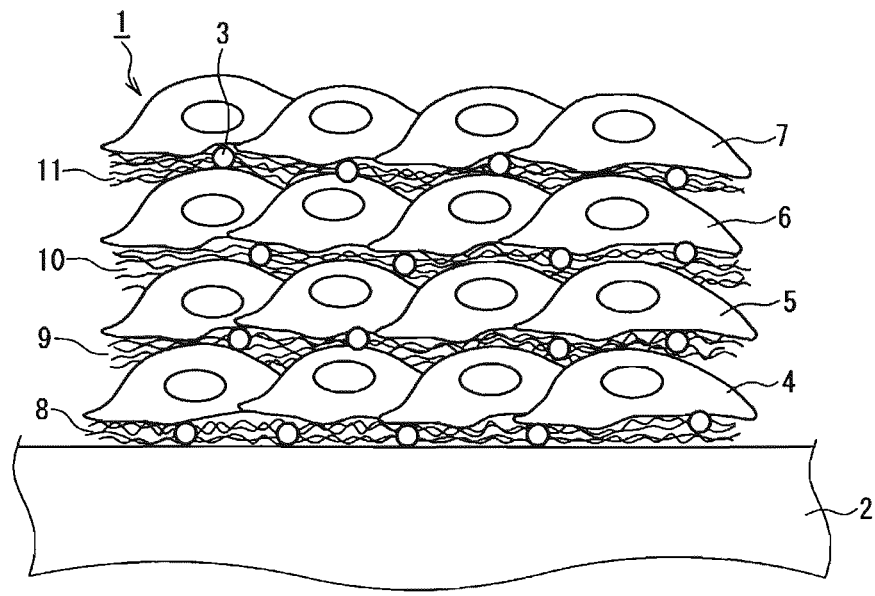
FIGS. 1A and 1B are schematic views showing exemplary three-dimensional cell culture constructs in the present invention.

[Biological Signal of Three-Dimensional (3D) Cell Culture Construct]

In the present invention, biological signals of a 3D cell culture construct refer to, for example, biological signals produced by cells cultured three-dimensionally. Examples of the biological signals of a 3D cell culture construct include biological signals produced individually or in a two-dimensional cell culture by cells constituting a 3D cell culture construct, and biological signals produced specifically by cells of a 3D cell culture construct. The example thereof further includes biological signals produced in a biological tissue that is a model target (mimetic target) of the 3D cell culture construct.

The present invention is based on findings that, by using a 3D cell culture construct that contains at least two cell layers laminated to each other and a sensor particle capable of detecting a biological signal, for example, it is possible to observe biological signals or the like produced from cells in the cell culture construct laminated three-dimensionally In other words, the present invention relates to a method for detecting a biological signal of a 3D cell culture construct, including: providing a 3D cell culture construct that contains at least two cell layers laminated to each other and a sensor particle capable of detecting a biological signal; and observing the sensor particle optically.

According to the method for detecting a biological signal of a 3D cell culture construct of the present invention, for example, it is possible to determine a diffused position of biological signals produced specifically in a biological tissue and to detect the biological signals quantitatively Thus, whether or not the 3D cell culture construct could form a tissue equivalent to the biological tissue can be inspected. Further, according to the method for detecting a biological signal of a 3D cell culture construct of the present invention, by using a 3D cell culture construct as a tissue model for example, it is possible to examine influences of various substances on a biological tissue. The method for detecting a biological signal of a 3D cell culture construct of the present invention preferably provides an effect that, for example, the method can be used as a testing/inspection/screening alternative to inspection/screening that are performed subsequent to conventional testing/inspection on safety or pharmacokinetics using laboratory animals and performed prior to administration to a human body, or an alternative to testing/inspection/screening using laboratory animals.

In the present invention, a substance functioning as a biological signal of a 3D cell culture construct is, for example, a substance produced individually or in a two-dimensional cell culture by cells constituting a 3D cell culture construct as a biological signal, a substance produced specifically by cells of a 3D cell culture construct as a biological signal, and a substance produced in a biological tissue that is a model target (mimetic target) of the 3D cell culture construct as a biological signal. Examples thereof include hormones, autacoids, neurotransmitters, cell growth factors, cytokines, biologically active substances, enzymes, and various ions. More specific examples thereof include nitrogen monoxide (NO), $Zn^{2+}$, $Ca^{2+}$, OH radical, protein-tyrosine phosphatase, active oxygen, $Mg^{2+}$, $Cl^-$, caspase, phosphodiesterase, $OCl^-$, histamine, dopamine, noradrenaline, serotonin and hydrogen peroxide.

[Sensor Particles]

In the present invention, the "sensor particle capable of detecting a biological signal" includes, for example, a particle capable of detecting the above-described substances functioning as a biological signal, and preferably includes a particle capable of reacting or bonding specifically with a biological signal substance and changing its luminescence property (e.g., a fluorescence property) by reacting or bonding with the biological signal substance. Further, the sensor particle capable of detecting a biological signal preferably is a non-cytotoxic particle.

In terms of concentrating a substance having a sensing function locally and/or improving a sensitivity of a quantitative evaluation and/or detecting a local change, it is preferable that the sensor particle contains a substance having a sensing function and a carrier for supporting the substance, and it is more preferable that the substance having a sensing function is supported inside the carrier. In the present invention, the "substance having a sensing function" includes, for example, a functional substance that changes its fluorescence properties such as an excitation wavelength, fluorescence wavelength and fluorescence intensity by reacting or bonding specifically with the substance functioning as a biological signal.

The substance having a sensing function can be selected appropriately by those skilled in the art in accordance with the type of the biological signal substance to be detected. Examples of the substance having a sensing function capable of detecting NO include 4,5-diaminofluorescein (DAF-2) (H. Kojima et al., Anal. Chem. 1998, 70, 2446), diaminorhodamine (DAR-4M, DAR-4MAM), 2,3-diaminonaphtalene (DAN), Diaminocyanine (DAC) and DAMBO-$^{pH}$. Examples of the substance having a sensing function capable of detecting $Ca^{2+}$ include 1-[6-Amino-2-(5-carboxy-2-oxazolyl)-5-benzofuranyloxy]-2-(2-amino-5-methylphenoxy) ethane-N,N,N',N'-tetraacetic acid, pentapotassium salt (Fura-2(1) and 1-[2-Amino-5-(2,7-dichloro-6-hydroxy-3-oxo-9-xanthenyl) phenoxy]-2-(2-amino-5-methylphenoxy)ethane-N,N,N',N'-tetraacetic acid (Fluo-3(2)) (A. Takahashi et at, Physiol. Rev. 1999, 79, 1089). Examples of the substance having a sensing function capable of detecting $Zn^{2+}$ include Dipicolycyanin (DIPCY), 1-[2-[5-(Dimethylamino)-1-naphthalenesulfonamido]ethyl]-1,4,7,10-tetraazacyclododecane, tetrahydrochioride, dehydrate (Dansylaminoethyl-cyclen) ZnAF-2F and ZnAF 2 DA Examples of the substance having a sensing function capable of detecting a chloride ion include N-Ethoxycarbonylmethyl-6-methoxyquinolinium bromide (MQAE). Examples of the substance having a sensing function capable of detecting OH radical and peroxynitrite include Hydroxyphenyl Fluorescein (HPF) and Aminophenyl Fluorescein (APF).

As to the sensor particle, in terms of causing a carrier to support the substance having a sensing function stably a surface of the carrier for supporting the substance having a sensing function is preferably laminated with a basic polymer layer and an acidic polymer layer alternately, more preferably laminated with plural basic polymer layers and plural acidic polymer layers alternately, and further preferably contains four or more basic polymer layers and four or more acidic polymer layers that are formed alternately.

Therefore, as one preferable configuration of the sensor particle in the present invention, the sensor particle contains a substance having a sensing function, a carrier for supporting the substance having a sensing function, and a basic polymer layer and an acidic polymer layer that are laminated alternately on a surface of the carrier, and wherein the carrier is a porous particle. With this configuration, it is possible to fix the sensor particle stably in the extracellular matrix by electrical interaction between charges on the surface of the sensor particle and the after-mentioned extracellular matrix, whereby the biological signals on the surface and inside of the 3D cell culture construct can be detected more accurately The sensor particle having a more preferable configuration can detect low-density biological signals (e.g., nano-mol order) produced by cells.

The basic polymer layer and the acidic polymer layer on the surface of the carrier can be produced by for example, a layer-by-layer (LBL) method in which a carrier supporting a substance having a sensing function is brought into contact with a basic polymer solution and an acidic polymer solution alternately so as to be laminated with plural layers. The basic polymer and the acidic polymer preferably are, for example, biocompatible polymers. Examples of the basic polymer include chitosan, chitin, polylysine and polydiallyldimethylammonium chloride. Examples of the acidic polymer include dextran sulfate, polyglutamic acid, polyaspartic acid, polystyrene sulfonic acid, poly-acrylic acid and polymethacrylic acid. Further, a polymer that is positively charged can be used as the basic polymer, and a polymer that is negatively charged can be used as the acidic polymer. Examples of the combination of the basic polymer and the acidic polymer include combinations of polylysine and dextran sulfate; and chitosan and dextran sulfate. Among these, the combination of chitosan and dextran sulfate is preferable, since they are biocompatible, less toxic and effectively prevent an outflow of the substance having a sensing function. The basic polymer and the acidic polymer can transmit the biological signal substance, and preferably, they are biodegradable. The carrier is not limited as long as it can support the substance having a sensing function. Preferably, the carrier can support the substance having a sensing function inside of the carrier, and examples thereof include porous particles such as silica, alumina and calcium phosphate. In terms of enabling the sensor particle to have more stable support and improved detection sensitivity, a mesoporous silica is preferable.

In terms of arranging the substance having a sensing function locally and in concentration in the 3D cell culture construct, the amount of the substance having a sensing function supported in the sensor particle is preferably in a range of 0.1 pg to 100 µg, and more preferably in a range of 1 pg to 1 µg per sensor particle.

Although the size of the sensor particle (particle size) can be determined appropriately depending on the size of cells, the particle size is, for example, 5 µm or less, preferably 3 µm or less, and more preferably 2 µm or less in terms of the sizes of cells and spaces between cell layers. Further, the particle size is, for example, 200 nm or more, and preferably 500 nm or more in terms of detecting biological signals sufficiently and/or causing the carrier to support the substance having a sensing function; and more preferably 1 µm or more, and further preferably 1.6 µm or more in terms of causing the sensor particle to be held between cell layers stably without being taken into cells. Therefore, in terms of causing the sensor particle to be held between cells layers more stably and to support a larger amount of the substance having a sensing function, the size of the sensor particle (particle size) is preferably 200 nm to 5 µm, more preferably 500 nm to 3 µm, further preferably 1 to 2 µm, and further more preferably 1.6 to 2 µm.

[Cell Layer]

Though not particularly limited, the number of the cell layers to be laminated in the 3D cell culture construct is preferably three or more layers, more preferably four or more layers, further preferably five or more layers, and further more preferably six or more layers in terms of allowing the cell culture construct to exhibit properties/functions more equivalent to those of a biological tissue of a human or the like. Though not particularly limited, an upper limit of the number of the cell layers to be laminated is, for example, 100 layers or less, 50 layers or less, 40 layers or less, 20 layers or less, and 10 layers or less.

Examples of the cells to be contained in the 3D cell culture construct include cells of humans and/or animals other than humans, and/or cells derived therefrom. Though not particularly limited, examples of the animals other than humans include primates (e.g., rhesus monkey), mice, rats and dogs. The human cells or cells derived therefrom are preferable in terms of allowing the cell culture construct to exhibit properties/functions more equivalent to those of a biological tissue of a human or the like.

Though not particularly limited, examples of the type of the cells include adhesive cells such as hepatocytes, vascular endothelial cells, fibroblasts, epidermic cells, epithelial cells, mammary glandular cells, myocytes, neurocytes, tissue stem cells, embryonic stem cells, bone cells, and immunocytes. One type or two or more types of cells can be used.

The cell layers in the 3D cell culture construct may be composed of one type or two or more types of cell layers. For example, in the case of forming a 3D cell culture construct of a blood vessel model, an uppermost cell layer may be formed of vascular endothelial cells, and plural cell layers that are placed below the uppermost cell layer may be formed of smooth muscle cells. The combination of the cell layers is not limited hereto.

[Extracellular Matrix]

It is preferable that the 3D cell culture construct of the present invention includes an extracellular matrix in addition to the cells and sensor particles. In the present invention, the extracellular matrix includes, for example, a biological substance filling a space outside of cells in an organism and playing a role as a skeletal outline, a role of providing a scaffold and/or a role of holding a biological factor as well as a substance capable of playing a role as a skeletal outline, a role of providing a scaffold and/or a role of holding a biological factor in an in vitro cell culture.

In terms of easier formation, easier thickness adjustment and higher efficiency of the 3D cell culture construct, the extracellular matrix of the present invention preferably contains a substance formed of a combination of a protein or polymer that has an RGD sequence (hereinafter, also referred to as "first substance having an RGD sequence") and a protein or polymer that interacts with the first substance having the RGD sequence (hereinafter, also referred to as "interactive second substance"), or a substance formed of a combination of a protein or polymer that is positively charged (hereinafter, also referred to as "positively charged first substance") and a protein or polymer that is negatively charged (hereinafter, also referred to as "negatively charged second substance"). Here, in the present invention, "interact" preferably means that, for example, the first substance and the second substance approach to each other to the extent that bonding, adhesion, adsorption, or electron transfer can occur chemically and/or physically between the first substance and the second substance through electrostatic interaction, hydrophobic interaction, hydrogen bonding, charge transfer interaction, formation of a covalent bond, specific interaction between proteins, van der Waals force, or the like.

(First Substance Having RGD Sequence)

The RGD sequence in the first substance having an RGD sequence, that is, a protein or polymer having an RGD sequence, refers to a generally known "Arg-Gly-Asp" sequence. In the present invention, a substance "having an RGD sequence" may be a substance that has the RGD sequence by nature or a substance to which the RGD sequence is bonded chemically It is preferable that the first substance having the RGD sequence is biodegradable and water-soluble. Examples of the protein having the RGD sequence include conventionally known adhesive proteins such as fibronectin, vitronectin, laminin, cadherin, and collagen. Further, the protein having the RGD sequence also may be collagen, gelatin, albumin, globulin, proteoglycan, enzymes, antibodies, etc., to which the RGD sequence is bonded. The polymer having the RGD sequence can be, for example, a naturally-occurring polymer and a synthetic polymer. Examples of the naturally-occurring polymer having the RGD sequence include water-soluble polypeptides, low molecular weight peptides, polyamino acids such as polylysine, polyester, sugars such as chitin and chitosan, polyurethane, polycarbonate, polyamide, and copolymers thereof. Examples of the synthetic polymer having the RGD sequence include a polymer or a copolymer having an RGD sequence with a linear, graft, comb, dendritic, or star structure, for example. Examples of the polymer or the copolymer include poly(N-isopropylacrylamide-co-polyacrylic acid), polyamideamine dendrimer, polyethylene oxide, poly($\epsilon$-caprolactam), polyacrylamide, and poly(methyl methacrylate-$\gamma$-polymethacrylate oxyethylene).

(Interactive Second Substance)

It is preferable that the interactive second substance is biodegradable and water-soluble. Among the interactive second substances, the protein that interacts with the first substance having the RGD sequence can be, for example, collagen, gelatin, proteoglycan, integrin, enzymes, and antibodies. Further, the polymer that interacts with the first substance having the RGD sequence is, for example, a naturally-occurring polymer and a synthetic polymer. Examples of the naturally-occurring polymer that interacts with the first substance having the RGD sequence include water-soluble polypeptides, low molecular weight peptides, elastin, polyamino acids, polyester, sugars such as heparin, heparan sulfate, dextran sulfate, polyurethane, poly-amide, polycarbonate, and copolymers thereof. Examples of the synthetic polymer that interacts with the first substance having the RGD sequence include a polymer or a copolymer having an RGD sequence with a linear, graft, comb, dendritic, or star structure, for example. Examples of the polymer or the copolymer include polyacrylic acid, polymethacrylic acid, polyethylene glycol-grafted-polyacrylic acid, poly(N-isopropylacrylamide-co-polyacrylic acid), polyamideamine dendrimer, polyethylene oxide, poly($\epsilon$-caprolactam), polyacrylamide, and poly(methyl methacrylate-$\gamma$-polymethacrylate oxyethylene).

The combination of the first substance having the RGD sequence and the interactive second substance is not limited particularly, and it preferably is a combination of different substances that interact with each other. Examples of the combination of the first substance and the second substance include combinations of fibronectin and gelatin; laminin and gelatin; fibronectin and dextran sulfate; polylysine and elastin; fibronectin and collagen; laminin and collagen; vitronectin and collagen; and RGD-bonded collagen or RGD-bonded gelatin and collagen or gelatin. Among these, the combination of fibronectin and gelatin and the combination of laminin and gelatin are preferable, and the combination of fibronectin and gelatin is more preferable. Note here that it is possible to use one type or two or more types of each of the first substance having the RGD sequence and the interactive second substance as long as they interact with each other.

(Positively Charged First Substance)

Among the positively charged first substances, the positively charged protein preferably is a water-soluble protein, for example. Examples of the water-soluble protein include basic collagen, basic gelatin, lysozyme, cytochrome c, peroxidase, and myoglobin. Among the positively charged first substances, the positively charged polymer can be, for example, a naturally-occurring polymer and a synthetic polymer. Examples of the naturally-occurring polymer include water-soluble polypeptides, low molecular weight peptides, polyamino acids, polyester, sugars such as chitin and chitosan, polyurethane, polyamide, polycarbonate, and copolymers thereof. Specific examples of the polyamino acids include polylysine such as poly($\alpha$-lysine), poly($\epsilon$-lysine), polyarginine, and polyhistidine. Examples of the synthetic polymer include a polymer or a copolymer with a linear, graft, comb, dendritic, or star structure, for example. Specific examples of the polymer or the copolymer include polydiallyldimethylammonium chloride, polyallylamine hydrochloride, polyethyleneimine, polyvinylamine, and polyamideamine dendrimer.

(Negatively Charged Second Substance)

Among the negatively charged second substances, the negatively charged protein preferably is a water-soluble protein, for example. Examples of the water-soluble protein include acidic collagen, acidic gelatin, albumin, globulin, catalase, $\beta$-lactoglobulin, thyroglobulin, $\alpha$-lactalbumin, and ovalbumin. Among the negatively charged second substances, the negatively charged polymer can be, for example, a naturally-occurring polymer and a synthetic polymer. Examples of the naturally-occurring polymer include water-soluble polypeptides, low molecular weight peptides, polyamino acids such as poly($\beta$-lysine), dextran sulfate, polyester, polyurethane, polyamide, polycarbonate, and copolymers thereof. Examples of the synthetic polymer include a polymer or a copolymer with a linear, graft, comb, dendritic, or star structure, for example. Specific examples of the polymer or the copolymer include polyester, polyacrylic acid, polymethacrylic acid, polystyrene sulfonate, polyacrylamidomethylpropane sulfonic acid, and terminal-carboxylated polyethylene glycol.

Examples of the combination of the positively charged first substance and the negatively charged second substance include combinations of chitosan and dextran sulfate; polyallylamine hydrochloride and polystyrene sulfonate; polydiallyldimethylammonium chloride and polystyrene sulfonate. Note here that it is possible to use one type or two or more types of each of the positively charged first substance and the negatively charged second substance as long as they interact with each other.

Further, as components of the extracellular matrix in the present invention, in terms of mimicking biological tissues more precisely, it is preferable to use components contained in natural in vivo) extracellular matrices. From the same reason, it is unnecessary to include chitosan, which sometimes is used as one alternative component of human extracellular matrices but is not present in a human body.

In the present invention, the 3D cell culture construct allows, for example, flexible lamination of plural kinds of cells, and/or easy control of the thickness of the cell layer and/or the extracellular matrix. Therefore, it is preferable that the 3D cell culture construct contains an extracellular matrix at least between cell layers, and can be produced by a process comprising: forming a cell layer by introducing a cell-containing solution; forming an extracellular matrix by introducing a first solution and a second solution alternately; forming the extracellular matrix and the cell layer alternately to laminate the cell layers; and placing the sensor particle capable of detecting a biological signal in at least one of layers positioned under a lowermost cell layer, between cell layers, and on an uppermost cell layer in the laminated cell layers, wherein a combination of an ingredient of the first solution and an ingredient of the second solution is a combination of a protein or polymer having an RGD sequence and a protein or polymer that interacts with the protein or polymer having the RGD sequence, or a combination of a protein or polymer that is positively charged and a protein or polymer that is negatively charged. The 3D cell culture construct used in the method for detecting a biological signal of a 3D cell culture construct of the present invention may he formed on a substrate. The substrate is not limited particularly, and conventionally known materials such as glass, various polymers, filter papers, metals, hydrogels can be used appropriately.

The layer to be in contact with the substrate in the 3D cell culture construct may he either the extracellular matrix layer or the cell layer. In the case where the substrate cannot serve as a scaffold of the cell layer, it is preferable to place the above-described extracellular matrix or apply a conventionally-known cell-culture coating on an arrangement area of the 3D cell culture construct.

In the method for detecting a biological signal of a 3D cell culture construct of the present invention, it is preferable that the sensor particles are placed in at least one of layers positioned under a lowermost cell layer, between cell layers, and on an uppermost cell layer in the 3D cell culture construct. In terms of determining the production portion and the diffused portion of biological signals easily, the sensor particles may be placed in any one of layers positioned under the lowermost cell layer, on the uppermost cell layer, and between the cell layers. Further, in terms of observing the spatial diffusion and dynamic images of the biological signals in one 3D cell culture construct, the sensor particles may be placed in plural layers positioned under the lowermost cell layer on the uppermost cell layer, and between the cell layers.

In the method for detecting a biological signal of a 3D cell culture construct of the present invention, in terms of determining the diffused portion of the biological signals easily, it is preferable to prepare a plurality of 3D cell culture constructs in which the sensor particles are placed in any one of layers positioned under the lowermost cell layer, between the cell layers and on the uppermost cell layer, and the layers placed with the sensor particles are different from one another, and to observe the sensor particles in each of the plurality of the 3D cell culture constructs optically. Further, the behavior of the biological signals may be analyzed based on the observation results.

A method for detecting a biological signal of a 3D cell culture construct using a plurality of 3D cell culture constructs will be described by taking as an example 3D cell culture constructs in which five cell layers are laminated. In the following example, a lowermost layer is a first layer, and an uppermost layer is a fifth layer. First, six kinds of 3D cell culture constructs, each containing sensor particles in any one of layers positioned under the first cell layer, between the first and second cell layers, between the second and third cell layers, between the third and fourth cell layers, between the fourth and fifth cell layers, and on the fifth cell layer, are prepared. Next, all the six kinds of the 3D cell culture constructs are subjected to a certain stimulus (e.g., stimulus of the test substance, etc), and then the sensor particles are observed optically In the case where the sensor particles are capable of detecting biological signals produced specifically from cells in the fifth cell layer, and the biological signals are detected in the 3D cell culture construct containing the sensor particles under the first cell layer, it is confirmed that the biological signals produced by the cells in the fifth cell layer are diffused to the first cell layer. Meanwhile, if the biological signals are detected in the 3D cell culture construct containing the sensor particles between the second and third cell layers, but the biological signals are not detected in the 3D cell culture construct containing the sensor particles under the first cell layer, it is confirmed that the biological signals are diffused to the vicinity of the second cell layer but are not diffused to the cell layer below the second layer.

In the method for detecting a biological signal of a 3D cell culture construct of the present invention, it is preferable that the optical observation of the sensor particle includes visualization and/or numeric conversion of the biological signal. In the method for observing the sensor particle optically, those skilled in the art can appropriately select a detection means for detecting the contained sensor particles, for example. Examples of the detection means include a fluorescence microscope, confocal laser scanning microscope, fluorescence spectrophotometer, confocal spectrophotometer and ultraviolet-visible spectrophotometer. By using a confocal laser scanning microscope, for example, biological signals produced by cells can be visualized and imaged, and preferably, the diffusion and/or the localization of specific signal molecules produced by the cells can be visualized. Therefore, the method for detecting a biological signal of a 3D cell culture construct of the present invention can be, for example, a powerful tool in research on differentiation induction or histogenesis in regenerative medicine. The "visualization of the biological signal" refers to, for example, an observation of the sensor particles in the 3D cell culture construct using a fluorescence microscope, confocal laser scanning microscope, etc., and/or capturing of a fluorescence microscope image. Further, the "numeric conversion of the biological signal" refers to, for example, measurement of a fluorescence spectrum, absorption spectrum, etc., of the sensor particle in the 3D cell culture construct using a fluorescence spectrophotometer, confocal spectrophotometer, ultraviolet-visible spectrophotometer, etc., and preferably refers to quantification using these spectra. Further, for example, by determining the diffused position of the biological signals using a confocal laser scanning microscope and measuring the spectra in that position, the biological signals can be quantified.

A method for detecting a biological signal of a 3D cell culture construct of the present invention and an embodiment of a 3D cell culture construct used in the method will be described with reference to FIGS. 1A and 1B. Note here that the present invention is not limited to the following embodiment.

Figure 1B:
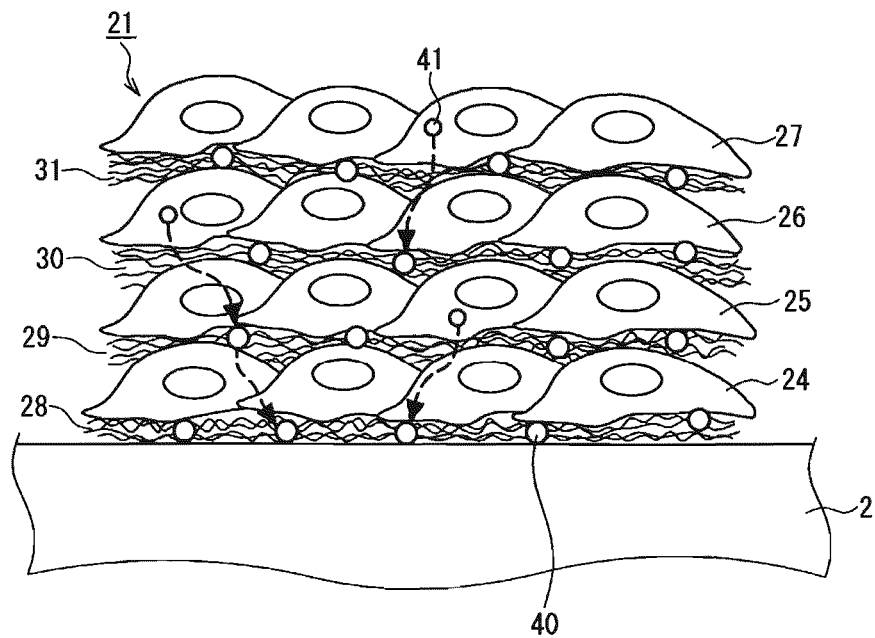

FIG. 1A is a view schematically showing an exemplary configuration of a 3D cell culture construct used in a method for detecting a biological signal of a 3D cell culture construct of the present invention. A 3D cell culture construct 1 shown in FIG. 1A is formed on a substrate 2, and includes sensor particles 3, cell layers 4 to 7 and extracellular matrix layers 8 to 11. The cell layers 4 to 7 are laminated via the extracellular matrix layers 8 to 11. The sensor particles 3 are placed in the extracellular matrix layers 8 to 11. As describe above, one type or two or more types of cells may be used in the cell layers 4 to 7. Further, the sensor particles 3 may be composed of sensor particles having the same sensing function or sensor particles having different sensing functions. By using the sensor particles having different sensing functions, it is possible to detect plural types of biological signals. The sensor particles having different sensing functions refer to, for example, sensor particles detecting different types of biological signals, different types of sensor particles detecting the same biological signal, or the like.

Next, the method for detecting a biological signal of a 3D cell culture construct of the present invention will be described by taking as an example the case of detecting a signal transduction of vascular endothelial cells in a blood vessel model. FIG. 1B is an exemplary configuration of a 3D cell culture construct of the blood vessel model in which four cell layers 24 to 27 are laminated on the substrate 2. The uppermost cell layer 27 is a cell layer of vascular endothelial cells, and plural cell layers 24 to 26 placed under the cell layer 27 are cell layers of smooth muscle cells. Extracellular matrix layers 28 to 31 and sensor particles 40 capable of detecting NO are placed between each cell layer. When a biological signal (NO) 41 is produced from the vascular endothelial cell, NO is transduced in the blood vessel model (indicated by an arrow), and only the sensor particle having received NO emits light. By observing the optical change of this sensor particle, it is possible to locally detect the production of the biological signals (NO) from the vascular endothelial cells and the signal transduction in the blood vessel model, for example. Further, since the sensor capable of detecting a biological signal is in the form of particle, local detection of the biological signals becomes easier. Further, by performing the optical observation of the sensor particles over time, it is possible to observe the spatial diffusion and dynamic images of the biological signals, for example. Furthermore, by locally detecting the production of the biological signals (NO) from the vascular endothelial cells and the signal transduction in the blood vessel model, it is possible to inspect the quality of the 3D cell culture construct as a blood vessel model and evaluate influences of drugs on blood vessels, for example.

Further, by causing the sensor particle to support Fura-4F, which is responsive to calcium ions, in place of DAF-2, the contraction of smooth muscle cells in a blood vessel model and the contraction of cardiac muscle cells in a cardiac muscle model can be evaluated, and hence this can be applied to the evaluation of therapeutic drug responses to arteriosclerosis and myocardial infarction. Further, by causing the sensor particle to support seminaphtho-rhodafluor-1-dye (SNARF-1), which is responsive to pH change, therapeutic drug responses to cancers and inflammatory reactions can be evaluated.

[Evaluation Method]

Since the method for detecting a biological signal of a 3D cell culture construct of the present invention allows, for example, the detection of biological signals produced in the biological tissue that is a model target (mimetic target) of the 3D cell culture construct, the method can be used for the evaluation of the 3D cell culture construct as the tissue model. Therefore, in another embodiment, the present invention relates to a method for evaluating a 3D cell culture construct, including; detecting a biological signal using the method for detecting a biological signal of a 3D cell culture construct of the present invention; and analyzing a cellular activity based on a detection result of the biological signal. The method for evaluating a 3D cell culture construct of the present invention can be, for example, a powerful tool in research on differentiation induction or histogenesis in regenerative medicine.

In the method for evaluating a 3D cell culture construct of the present invention, the analysis of the cellular activity includes, for example, the determination of the diffused position of biological signals and the quantification of biological signals. The method for evaluating a 3D cell culture construct of the present invention includes the determination of the diffused position of biological signals produced specifically in a biological tissue and/or the quantitative detection of the biological signals produced specifically. Further, on an as-needed basis, the method may include the evaluation judging whether or not the 3D cell culture construct could form a tissue equivalent to the targeted biological tissue based on these results. The determination of the diffused position and the quantification can be performed by, for example, a fluorescence microscope, confocal laser scanning microscope, fluorescence spectrophotometer, confocal spectrophotometer or ultraviolet-visible spectrophotometer.

Further, in still another embodiment, the present invention relates to a method for evaluating a test substance with respect to an organism, including: bringing a 3D cell culture construct into contact with a test substance selected from the group consisting of compounds, medical compositions, cosmetics and foods; and detecting a biological signal of the 3D cell culture construct using the method for detecting a biological signal of a 3D cell culture construct of the present invention. According to the evaluation method of the present invention, for example, it is possible to perform testing/inspection/screening on safety and pharmacokinetics in the fields of medicine, pharmaceutical production, cosmetics, foods, environments, etc. Further, according to the method for evaluating a test substance with respect to an organism of the present invention, for example, it preferably provides an effect that these testing/inspection/screening bring highly-reliable results reflecting the biology of a human body more precisely. In the method for evaluating a test substance with respect to an organism of the present invention, the detection of the biological signals includes, for example, the determination of the diffused position of biological signals and the quantification of biological signals. The "evaluation of a test substance with respect to an organism" in the present invention refers to, for example, an evaluation of influences of a test substance on an organism.

The detection of the biological signals may be performed at any time before, during or after contacting the 3D cell culture construct and the test substance for example, or performed before, during and after the contact. Further, the detection may be performed over time from before the contact to after the contact.

[Detection Kit]

A "detection kit" in the present invention includes, for example, a product including a reagent, material, tool and equipment used for a predetermined inspection and at least one manual (instruction manual) about the inspection. In another embodiment, the present invention relates to a detection kit used in the detection method of the present invention (hereinafter, also referred to as "detection kit of the present invention"), including a 3D cell culture construct containing at least two cell layers laminated to each other and a sensor particle capable of detecting a biological signal. According to the detection kit of the present invention, the method for detecting a biological signal of a 3D cell culture construct of the present invention can be performed more simply. The detection kit of the present invention can be used for, for example, the visualization of cellular functions, imaging of biological signals such as determination of the diffused position, quantitative analysis, etc. The 3D cell culture construct in the detection kit is the same as that used in the above-described detection method of the present invention. The detection kit further may include an instruction manual in which a method for detecting a biological signal of a 3D cell culture construct is described, etc.

[Method for Producing 3D Cell Culture Construct]

In still another embodiment, the present invention relates to a method for producing a 3D cell culture construct (hereinafter, also referred to as "production method of the present invention"), including: forming a cell layer by introducing a cell-containing solution; forming an extracellular matrix by introducing a first solution and a second solution alternately; forming the extracellular matrix and the cell layer alternately to laminate the cell layers; and placing the sensor particle capable of detecting a biological signal in at least one of layers positioned under a lowermost cell layer, between cell layers, and on an uppermost cell layer, wherein a combination of an ingredient of the first solution and an ingredient of the second solution is a combination of a protein or polymer having an RGD sequence and a protein or polymer that interacts with the protein or polymer having the RGD sequence, or a combination of a protein or polymer that is positively charged and a protein or polymer that is negatively charged.

According to the production method of the present invention, it is possible to produce a 3D cell culture construct that can be used in the method for detecting a biological signal of a 3D cell culture construct of the present invention, the 3D cell culture construct containing at least two cell layers laminated to each other and a sensor particle capable of detecting a biological signal. Therefore, in still another embodiment, the present invention relates to a 3D cell culture construct produced by the production method of the present invention, which contains at least two cell layers laminated to each other and a sensor particle capable of detecting a biological signal. In the 3D cell culture construct of the present invention, the sensor particle preferably is placed in at least one of layers positioned under the lowermost cell layer, between the cell layers, and on the uppermost cell layer in the 3D cell culture construct.

[Formation of Extracellular Matrix]

The formation of the extracellular matrix in the production method of the present invention is performed by, for example, introducing the first solution and the second solution alternately on the cell layer on the substrate. The first solution and the second solution can be introduced by for example, bringing the cell layer into contact with the first solution and the second solution by, for example, an application, immersion, dropping, spraying, etc.

The thickness of the extracellular matrix thin film formed by introducing the first solution and the second solution once is about 1 to 20 nm. By introducing these solutions repeatedly an extracellular matrix layer having a desired thickness can be formed. Further, the thickness of the extracellular matrix layer to be formed can be adjusted by adjusting the content of the first substance and the content of the second substance in the first solution and the second solution, respectively. These methods allow the extracellular matrix layer to have a thickness of for example, 1 to 1000 nm, preferably 1 to 300 nm, and more preferably 5 to 100 nm.

The ingredient contained in the first solution can be selected from the first substance having the RGD sequence and the positively charged first substance described above. The ingredient contained in the second solution can be selected from the interactive second substance and the negatively charged second substance described above. The preferable combinations of the ingredient of the first solution and the ingredient of the second solution are as described above. Here, the ingredient of the first solution or the ingredient of the second solution refers to a substance dissolved and/or dispersed in a liquid medium of each solution.

The first solution and the second solution can be prepared by, for example, dissolving or dispersing the above-described first substance and the second substance in a solvent or a dispersion medium, respectively The content of the first substance in the first solution and the content of the second substance in the second solution are preferably from 0.0001 to 1 mass %, more preferably from 0.01 to 0.5 mass %, and more preferably from 0.02 to 0.1 mass %, for example.

Though not particularly limited, the solvent or dispersion medium in each of the first solution and the second solution (hereinafter, also referred to as "solvent" simply) is, for example, an aqueous solvent such as water and a buffer solution. Specific examples of the buffer solution include Tris buffer solutions such as Tris-HCl buffer solution, phosphate buffer solution, HEPES buffer solution, citric acid-phosphate buffer solution, glycylglycine-sodium hydroxide buffer solution, Britton-Robinson buffer solution and GTA buffer solution. Though not particularly limited, the pH of the solvent is, for example, 3 to 11, preferably 6 to 8, and more preferably 7.2 to 7.4.

The first solution and the second solution may contain a salt such as sodium chloride, calcium chloride, sodium hydrogen carbonate, sodium acetate, sodium citrate, potassium chloride, sodium hydrogen phosphate, magnesium sulfate and sodium succinate. One type or two or more types of salts may be contained in the solutions. Both or either one of the first solution and the second solution may contain salts. Though not particularly limited, the concentration of the salt is, for example, $1 \times 10^{-6}$ to 2 M, preferably $1 \times 10^{-4}$ to 1 M, and more preferably $1 \times 10^{-4}$ to 0.05 M.

On an as-needed basis, the first solution and the second solution may further contain, for example, a cell growth factor, cytokine, chemokine, hormone, or biologically active peptide; medical composition such as a therapeutic agent for treating a disease, a prophylactic agent for preventing a disease, an inhibitor for inhibiting a disease, an antibacterial agent, or an antiinflammatory agent.

[Formation of Cell Layer]

The formation of the cell layer in the production method of the present invention is performed by introducing a cell-containing solution on a predetermined region on the substrate and/or on the extracellular matrix formed on a predetermined region. The cell-containing solution is introduced in the same manner as the first solution and the second solution.

In the formation of the cell layer, after introducing the cell-containing solution, the solution thus introduced preferably is incubated for a predetermined time. This incubation allows the arranged cells to grow two-dimensionally (planar direction), whereby the cells can be formed in a monolayer with ease. The conditions of the incubation are not particularly limited, and can be determined as appropriate depending on the type of cells. The general conditions thereof are as follows: the temperature is, for example, 4 to 60° C., preferably 20 to 40° C., and more preferably 30 to 37° C.; the period is, for example, 1 to 168 hours, preferably 3 to 24 hours, and more preferably 3 to 12 hours. Further, a culture medium to be used in the cell culture is not particularly limited, and can be determined as appropriate depending on the type of cells. Examples of the culture medium include Eagle's MEM medium, Dulbecco's Modified Eagle's medium (DMEM), Modified Eagle medium (MEM), Minimum Essential medium, RDMI, GlutaMax medium and serum-free medium.

The density of cells in the cell-containing solution is preferably $(1.0) \times 10^4$ to $(1.0) \times 10^9$ cells/mL, more preferably $(1.0) \times 10^5$ to $(1.0) \times 10^8$ cells/mL, and further preferably $(1.0) \times 10^6$ to $(1.0) \times 10^7$ cells/mL in terms of forming the cell layers effectively As a medium of the cell-containing solution, the above-described culture medium and/or Tris buffer solution, phosphate buffer solution, HEPES, PBS or the like can be used.

[Placement of Sensor Particles]

The sensor particles may be placed in the 3D cell culture construct by mixing the sensor particles into the first solution, the second solution and the cell-containing solution for example, or placed under the lowermost cell layer, between the cell layers, on the uppermost cell layer, etc., by dispersing the particles into another solvent, for example. Examples of the solvent in which the sensor particles are dispersed include the solvents described above as the solvents used for the first solution, the second solution and the cell-containing solution. The placement position of the sensor particles can be determined as appropriate depending on the purpose, and for example, they may be placed evenly in the entire 3D cell culture construct or locally in the 3D cell culture construct. Further, the sensor particles may be ones having the same sensing function or ones having different sensing functions. In the case of using the sensor particles having different sensing functions, it is possible to detect plural types of biological signals.

Hereinafter, the present invention will be described further by way of example. Note here that the present invention is, when interpreted, not limited to the following example.

EXAMPLE

[Production of Sensor Particles]

Mesoporous silica particles (average particle diameter: 1.6 μm) were used as a carrier; and 4,5-diaminofluorescein (DAF-2), which is a substance emitting light by detecting NO, was used as a substance having a sensing function. First, the mesoporous silica particles were immersed in a 25 μM DAF-2 solution, which allowed the particles to support DAF-2 inside of the particles. After the mesoporous silica particles each supporting DAF-2 were washed, they were immersed in a chitosan solution (1 mg/mL chitosan, 1M NaCl, pH1) and a dextran sulfate solution (1 mg/mL dextran sulfate, 1M NaCl, pH7) alternately for six times. Thus, the sensor particle in which six each of chitosan layers and dextran sulfate layers were laminated alternately on the surface of the mesoporous silica particle was produced. The thickness of the chitosan/dextran sulfate layers laminated on the surface of the silica particle was about 130 nm, and the average particle diameter of the obtained sensor particle was about 1.8 μm.

Figure 2A:
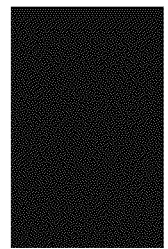
FIG. 2A is an exemplary photograph taken through an observation of a sensor particle dispersion.
Figure 2B:
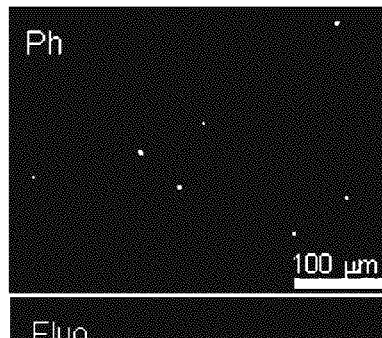
FIG. 2B is an exemplary photograph taken through the observation of the sensor particle dispersion.
Figure 2C:
FIG. 2C is an exemplary photograph taken through the observation of the sensor particle dispersion.
Figure 2D:
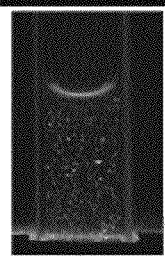
FIG. 2D is an exemplary photograph taken through the observation of the sensor particle dispersion.
Figure 2E:
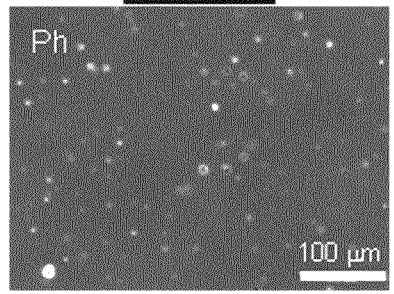
FIG. 2E is an exemplary photograph taken through the observation of the sensor particle dispersion.
Figure 2F:
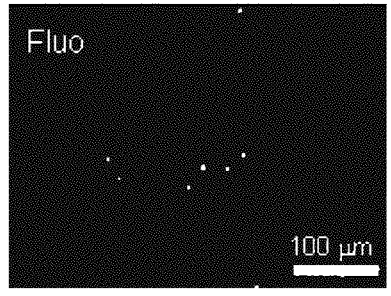
FIG. 2F is an exemplary photograph taken through the observation of the sensor particle dispersion.

The detectability of NO by the sensor particles was examined. First. NOC-7 (1-Hydroxy-2-oxo-3-(N-methyl-3-3aminopropyl)-3-methyl-1-triazene) serving as a NO donor was dissolved in a 50 mM Tris buffer solution (pH 7.4) to prepare a NOC-7 solution (50 nM NOC-7). Subsequently the NOC-7 solution was added to a sensor particle dispersion (0.5 M NaCl, pH7), and states of the sensor particle dispersion before and after the addition of the NOC-7 solution were observed using a phase-contrast microscope and fluorescence microscope. The results are shown in FIGS. 2A to 2F. FIGS. 2A, 2B and 2C are photographs of the sensor particle dispersion before the addition of the NOC-7 solution taken by a digital camera, phase-contrast microscope (×40) and fluorescence microscope (×40), respectively. FIGS. 2D, 2E and 2F are photographs of the sensor particle dispersion after the addition of the NOC-7 solution taken by the digital camera, phase-contrast microscope (×40) and fluorescence microscope (×40), respectively As shown in FIGS. 2A to 2F, the sensor particles showed their strong fluorescence in the presence of NO. Therefore, it was confirmed that the sensor particles could detect NO.

[Production of 3D Cell Culture Construct]

In the following manner, the 3D cell culture construct was produced in which human umbilical vein endothelial cells (HUVEC) were laminated on human smooth muscle cells (SMC) on the substrate and the extracellular matrix and sensor particles were placed between the SMC layer and the HUVEC layer. First, a substrate was immersed in an undercoat film solution (0.2 mg/mL fibronectin, 50 mM Tris buffer solution (pH 7.4)), so that an undercoat film was formed on the substrate. Next, a solution containing SMC cells ($4.0 \times 10^4$ cells/mL human smooth muscle cells, 50 mM Tris buffer solution (pH 7.4)) was placed on the undercoat film and incubated overnight by a cell culture incubator (37° C., 5% $CO_2$) for adhering the cells (SMC layer). Subsequently, the SMC layer on the substrate was immersed in a first solution for forming extracellular matrix (0.2 mg/mL fibronectin, 50 mM Tris buffer solution (pH 7.4)) and a second solution for forming extracellular matrix (0.2 mg/mL gelatin, 50 mM Tris buffer solution (pH 7.4)). By repeating the immersion in the first solution (fibronectin) and the second solution (gelatin) alternately for ten times, a fibronectin-gelatin thin film (extracellular matrix) was formed on the surface of the SMC layer. Immediately after that, the sensor particles were placed on the extracellular matrix. Then, a solution containing HUVEC cells ($6.0 \times 10^4$ cells/mL human umbilical vein endothelial cells, 50 mM Tris buffer solution (pH 7.4)) was placed thereon and incubated overnight by the cell culture incubator (37° C., 5% $CO_2$) for adhering the cells (HUVEC layer).

Further, as a reference example, a cell culture construct was produced in which a HUVEC layer was formed on a substrate and sensor particles were placed on the surface. First, the substrate is immersed in the undercoat film solution, thus an undercoat film was formed on the substrate. Next, the solution containing HUVEC cells was placed on the undercoat film and incubated overnight by the cell culture incubator (37° C., 5% $CO_2$) for adhering the cells (HUVEC layer). Then, the sensor particles were placed on the surface of the HUVEC layer. Note here that the same undercoat film solution and the same solution containing HUVEC cells as those described above were used in this reference example.

Figure 3A:
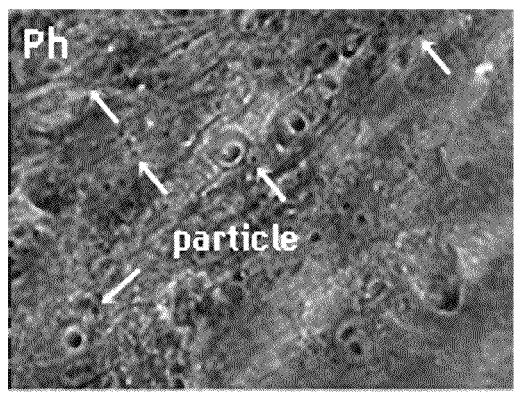
FIG. 3A is an exemplary microphotograph taken through the observation of the three-dimensional cell culture construct.
Figure 3B:
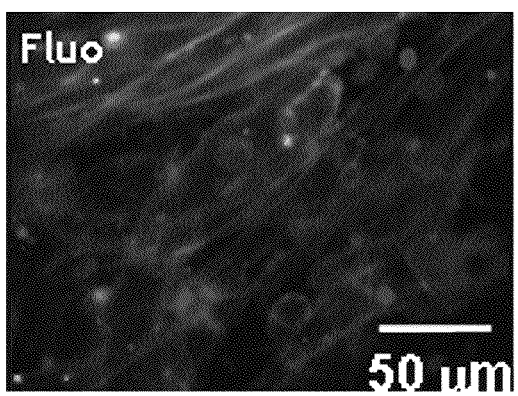
FIG. 3B is an exemplary microphotograph taken through the observation of the three-dimensional cell culture construct.
Figure 3C:
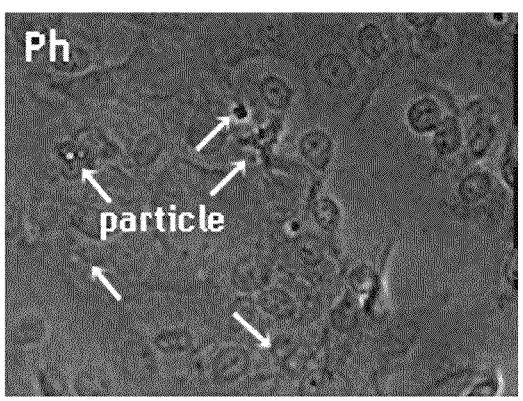
FIG. 3C is an exemplary microphotograph taken through the observation of a reference example.
Figure 3D:
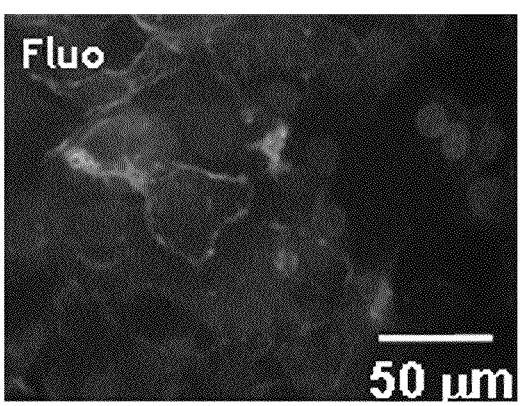
FIG. 3D is an exemplary microphotograph taken through the observation of the reference example.

The thus obtained 3D cell culture construct and the cell culture construct of the reference example were observed using the phase-contrast microscope and confocal laser scanning microscope. The microphotographs are shown in FIGS. 3A to 3D. Note here that F-actins were stained with phalloidin-rhodamine and cell nuclei were stained with DAPI (4'6-diamino-2-2phenylidole). FIG. 3A is a photograph of the 3D cell culture construct taken by the phase-contrast microscope (×60), FIG. 3B is a photograph of the 3D cell culture construct taken by a confocal fluorescence microscope (×60). FIG. 3C is a photograph of the cell culture construct of the reference example taken by the phase-contrast microscope (×60), and FIG. 3D is a photograph of the cell culture construct of the reference example taken by the confocal fluorescence microscope (×60). Note here that the photograph of FIG. 3B was taken for focusing the SMC layer and the sensor particles placed between the layers for the observation. In FIGS. 3A and 3C, circular substances indicated by white arrows are sensor particles. In FIGS. 3B and 3D, substances emitting yellow-green light are sensor particles.

In the photograph of FIG. 3D, cobblestone-shaped cells derived from HUVEC and sensor particles were observed. On the other hand, in the photograph of FIG. 3B, elongated cells, which are characteristic of SMC, and sensor particles were observed, but the cobblestone-shaped cells derived from HUVEC laminated on the SMC layer were not observed. As just described, since the HUVEC layer was not observed in the photograph of FIG. 3B, it was confirmed that the sensor particles were supported between the SMC layer and the HUVEC layer. Further, as shown in FIGS. 3B and 3D, both the cells SMC and HUVEC showed no change in their cellular configuration. Therefore, it was confirmed that the sensor particles placed in the 3D cell culture construct did not affect the cells (SMC and HUVEC), and hence they were non-cytotoxic.

[Detection of Biological Signals of the 3D Cell Culture Construct]

Figure 4A:
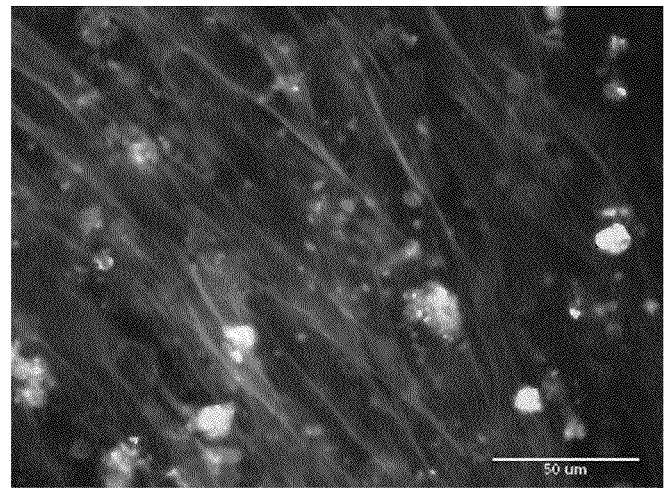
FIG. 4A is an exemplary microphotograph taken through the observation of the three-dimensional cell culture construct.
Figure 4B:
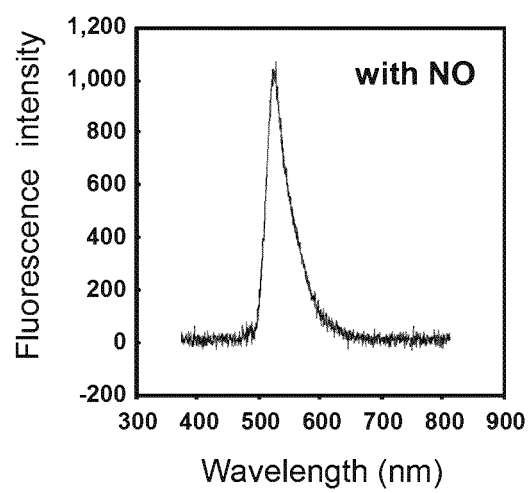
FIG. 4B is an exemplary fluorescence spectrum of a sensor particle in the three-dimensional cell culture construct.
Figure 4C:
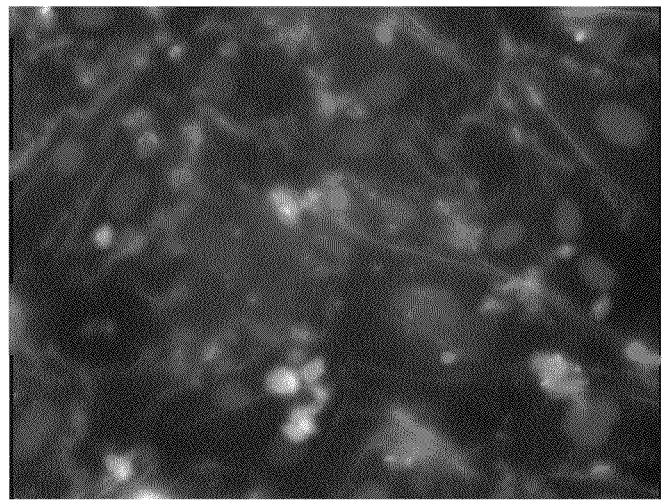
FIG. 4C is an exemplary microphotograph taken through the observation of a cell culture construct of the reference example.
Figure 4D:
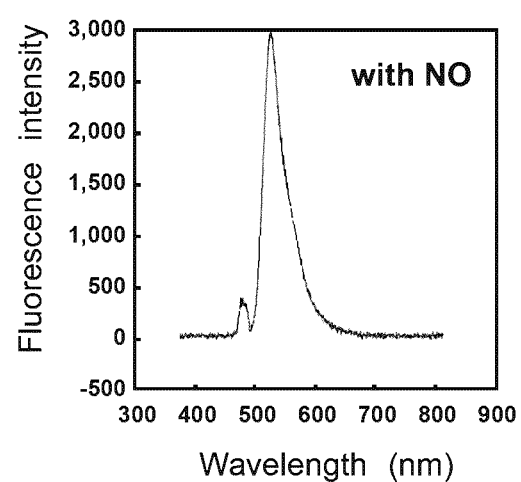
FIG. 4D is an exemplary fluorescence spectrum of a sensor particle in the cell culture construct of the reference example.

The NOC-7 solution was dropped on the above-described 3D cell culture construct and cell culture construct of the reference example for observing the sensor particles using the confocal laser scanning microscope and measuring fluorescence spectra of the sensor particles. The results are shown in FIGS. 4A to 4D. Note here that the same NOC-7 solution as that used in the detection of the sensor particles was used. FIG. 4A is a photograph of the 3D cell culture construct taken by the confocal fluorescence microscope (×40), FIG. 4B shows a fluorescence spectrum of the 3D cell culture construct, FIG. 4C is a photograph of the cell culture construct of the reference example taken by the confocal fluorescence microscope (×40), and FIG. 4D shows a fluorescence spectrum of the cell culture construct of the reference example. Note here that the photograph of FIG. 4A was taken for focusing the SMC layer and the sensor particles placed between the SMC layer and the layer for the observation.

In the photograph of FIG. 4A, the elongated cells, which are characteristic of SMC, and sensor particles were observed, but the cobblestone-shaped cells derived from HUVEC laminated on the SMC layer were not observed. Thus, it was confirmed that the sensor particles were supported between the SMC layer and the HUVEC layer. Further, since yellow-green fluorescence was observed, it was confirmed that the sensor particles supported between the layers could detect NO.

In both of FIGS. 4B and 4D, peaks appeared in the vicinity of 515 nm. These peaks indicate that DAF-2 supported inside the sensor particle was changed to DAF-2T (triazolflorescein) by receiving NO. Therefore, it was confirmed that NO could be detected by the sensor particles placed in the 3D cell culture construct and spectra of the sensor particles could be measured. Further, since the spectrum of DAF-2T (substance having a sensing function) inside the sensor particle placed in the 3D cell culture construct could be measured, it is considered that the biological signals of the 3D cell culture construct can be evaluated quantitatively.

[Productions of Calcium-Responsive Sensor Particles and pH-Responsive Sensor Particles]

Mesoporous silica particles (average particle diameter: 1.6 μm) were used as a carrier; and Fura-4F, which is a calcium-ion-responsive substance, and SNARF-1, which is a pH-responsive substance, were used as substances having a sensing function. First, the mesoporous silica particles were immersed in a 24 μM Fura-4F solution and a 24 μM SNARF-1 solution for 24 hours in each solution. Thereby both of the responsive substances were supported inside the particles. After the mesoporous silica particles each supporting both of the responsive substances were washed, they were immersed in a chitosan solution (1 mg/mL chitosan, 1M NaCl, pH1) and a dextran sulfate solution (1 mg/mL dextran sulfate, 1M NaCl, pH7) alternately for six times. Thus, the sensor particle in which six each of chitosan layers and dextran sulfate layers were laminated alternately on the surface of the mesoporous silica particle was produced. The thickness of the chitosan/dextran sulfate layers laminated on the surface of silica particle was about 130 nm, and the average particle diameter of the obtained sensor particle was about 1.8 μm.

Figure 5A:
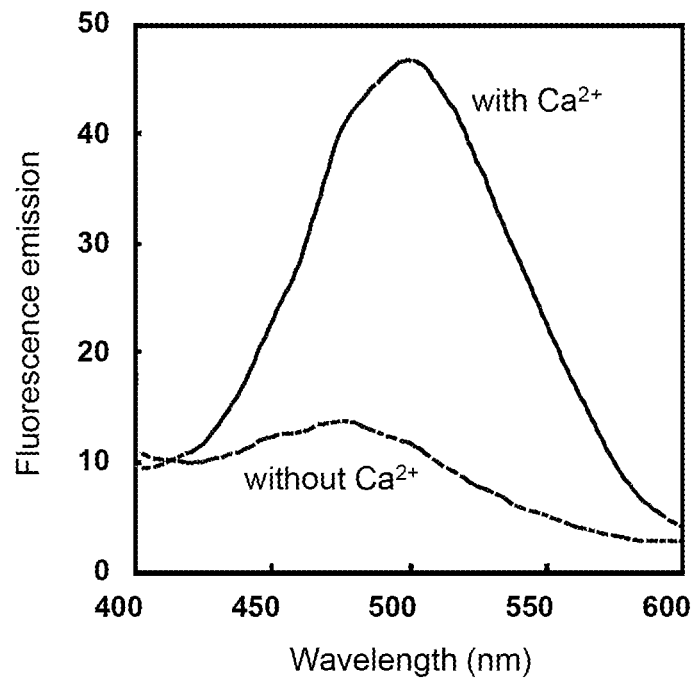
FIG. 5A is an exemplary fluorescence spectrum of a calcium-ion-responsive sensor particle produced in EXAMPLE.
Figure 5B:
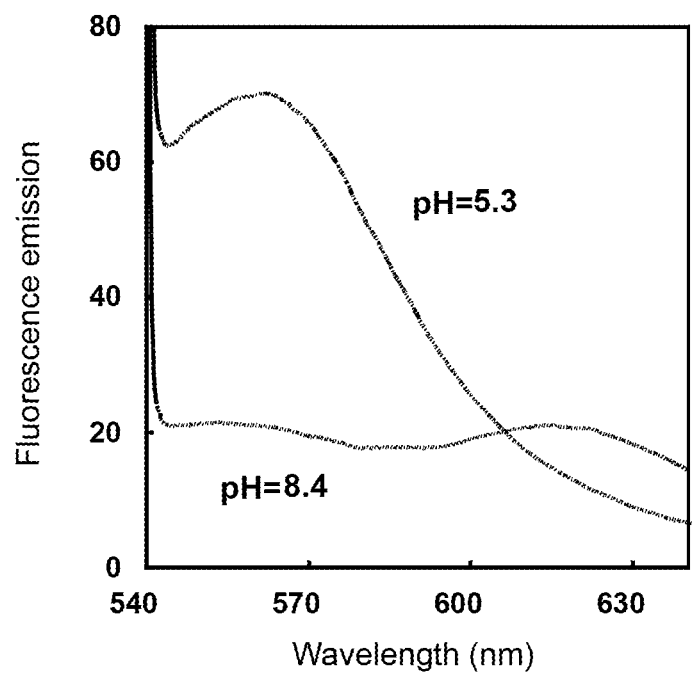
FIG. 5B is an exemplary fluorescence spectrum of a pH-responsive sensor particle produced in EXAMPLE.

The detectabilities of calcium ions and pH change by the sensor particles were examined. The sensor particles supporting Fura-4F were dissolved in a 1 M calcium chloride solution (50 mM Tris buffer solution, pH 7.4) so that the concentration of the particles became about 1 mg/mL. Then, fluorescence spectra were observed. The result was shown in FIG. 5A. It was confirmed that the sensor particles emitted light only in the presence of calcium ions. Further, the pH change was detected in the following process. A sensor particle dispersion in which SNARE-1 was supported in the concentration of 1 mg/mL was dissolved in 50 mM each of potassium dihydrogenphosphate buffer solutions that were adjusted at pH 5.3 and pH 8.5. Then, fluorescence spectra were measured. The result was shown in FIG. 5B. Under an acidic condition (pH 5.3), strong fluorescence was observed in 580 mn; whereas, under a basic condition (pH 8.5), fluorescence was observed in 640 nm. From these results, it was confirmed that the sensor particles emitting fluorescence by responding to calcium ions and pH change were produced.

INDUSTRIAL APPLICABILITY

As described above, the present invention is useful in the fields of, for example, medicine, pharmaceutical production, cosmetics, foods, regenerative medicine and environmental protection.

DESCRIPTION OF REFERENCE NUMERALS 1, 21 3D cell culture construct
2 substrate
3, 40 sensor particle
4-7, 24-27 cell layer
8-11, 28-31 extracellular matrix
41 biological signal (NO molecule)

The invention claimed is:

1. A method for detecting a biological signal of a construct that is produced by a layer-by-layer (LBL) method, comprising:
    providing a construct that is produced by an LBL method and contains at least two cell layers, an extracellular matrix, and a sensor particle capable of detecting a biological signal; and
    observing the sensor particle optically,
    wherein the construct is provided so that the extracellular matrix is formed between the cell layers, thereby laminating the cell layers to one another, and
    wherein the construct is provided so that the sensor particle is placed in the extracellular matrix between the cell layers.

2. The method according to claim 1,
    wherein the sensor particle contains a substance having a sensing function, a carrier for supporting the substance having a sensing function, and a biocompatible basic polymer layer and a biocompatible acidic polymer layer that are laminated alternately on a surface of the carrier, and
    the carrier is a porous particle.

3. The method according to claim 1, wherein the optical observation of the sensor particle includes visualization and/or numeric conversion of the biological signal.

4. The method according to claim 1,
    wherein the extracellular matrix includes a combination of a protein or polymer having an RGD sequence and a protein or polymer that interacts with the protein or polymer having the RGD sequence, or a combination of a protein or polymer that is positively charged and a protein or polymer that is negatively charged.

5. The method according to claim 1,
    wherein the construct is capable of being produced by a process, comprising:
        forming a cell layer by introducing a cell-containing solution;

forming an extracellular matrix by introducing a first solution and a second solution alternately;

forming the extracellular matrix and the cell layer alternately to laminate the cell layers; and placing the sensor particle capable of detecting a biological signal between cell layers, wherein a combination of an ingredient of the first solution and an ingredient of the second solution is a combination of a protein or polymer having an RGD sequence and a protein or polymer that interacts with the protein or polymer having the RGD sequence, or a combination of a protein or polymer that is positively charged and a protein or polymer that is negatively charged.

6. The method according to claim 1, wherein the sensor particle contains a substance having a sensing function, a carrier for supporting the substance having a sensing function, and a basic polymer layer and an acidic polymer layer that are laminated alternately on a surface of the carrier.

7. A method for evaluating a construct that is produced by a layer-by-layer (LBL) method, comprising:

detecting a biological signal using the method according claim 1; and analyzing a cellular activity based on a detection result of the biological signal.

8. A method for evaluating a test substance with respect to an organism, comprising:

bringing a construct that is produced by a layer-by-layer (LBL) method into contact with a test substance selected from the group consisting of compounds, medical compositions, cosmetics and foods; and detecting a biological signal of the construct using the method according to claim 1.

* * * * *